United States Patent
Davidson et al.

(10) Patent No.: US 7,505,062 B2
(45) Date of Patent: *Mar. 17, 2009

(54) SYSTEM AND METHOD FOR DISPLAYING AN IMAGE STREAM

(75) Inventors: Tal Davidson, Haifa (IL); Reuven Schreiber, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 768 days.

This patent is subject to a terminal disclaimer.

(21) Appl. No.: 10/364,508

(22) Filed: Feb. 12, 2003

(65) Prior Publication Data

US 2003/0151661 A1    Aug. 14, 2003

Related U.S. Application Data

(60) Provisional application No. 60/355,796, filed on Feb. 12, 2002.

(51) Int. Cl.
*H04N 7/18* (2006.01)
*G06F 3/48* (2006.01)

(52) U.S. Cl. .................................... 348/77; 715/838

(58) Field of Classification Search ............ 348/77, 348/45, 46, 131, 809, 564, 565; 715/838; 600/424, 476; 386/46

See application file for complete search history.

(56) References Cited

U.S. PATENT DOCUMENTS

| | | | |
|---|---|---|---|
| 4,243,652 A | 1/1981 | Francis | |
| 4,278,077 A | 7/1981 | Mizumoto | |
| 4,698,664 A | 10/1987 | Nichols et al. | |
| 5,381,784 A | 1/1995 | Adair | |
| 5,603,687 A | 2/1997 | Hori et al. | |
| 5,604,531 A | 2/1997 | Iddan et al. | |
| 5,697,885 A | 12/1997 | Konomura et al. | |
| 5,993,378 A | 11/1999 | Lemelson | |
| 6,173,317 B1 | 1/2001 | Chaddha | |
| 6,208,354 B1 | 3/2001 | Porter | |
| 6,240,312 B1 | 5/2001 | Alfano et al. | |
| 6,289,165 B1 * | 9/2001 | Abecassis | 386/46 |
| 6,504,990 B1 * | 1/2003 | Abecassis | 386/46 |
| 6,904,308 B2 * | 6/2005 | Frisch et al. | 600/424 |
| 6,976,229 B1 * | 12/2005 | Balabanovic et al. | 715/838 |
| 7,324,673 B1 | 1/2008 | Yamanaka et al. | |
| 2001/0015753 A1 | 8/2001 | Myers | |
| 2001/0035902 A1 | 11/2001 | Iddan et al. | |

(Continued)

FOREIGN PATENT DOCUMENTS

DE    344 0177    5/1986

(Continued)

OTHER PUBLICATIONS www.dynapel.com, Motion Perfect® product literature, printed Jul. 22, 2003.

(Continued)

*Primary Examiner*—Gims S Philippe
(74) *Attorney, Agent, or Firm*—Pearl Cohen Zedek Latzer, LLP

(57) ABSTRACT

A system and method may display an image stream, where an original image stream may be divided into two or more subset images streams, each subset image stream being displayed simultaneously or substantially simultaneously. The images may be collected from an ingestible capsule traversing the GI tract.

13 Claims, 3 Drawing Sheets

U.S. PATENT DOCUMENTS

| | | | |
|---|---|---|---|
| 2002/0103417 | A1 | 8/2002 | Gazdzinski |
| 2002/0109774 | A1 | 8/2002 | Meron et al. |
| 2002/0177779 | A1* | 11/2002 | Adler et al. .................. 600/476 |
| 2003/0086596 | A1 | 5/2003 | Hipp et al. |
| 2003/0174208 | A1* | 9/2003 | Glukhovsky et al. ........ 348/131 |
| 2004/0027500 | A1* | 2/2004 | Davidson et al. ............ 348/809 |
| 2004/0249291 | A1 | 12/2004 | Honda et al. |
| 2005/0038321 | A1 | 2/2005 | Fujita et al. |
| 2006/0108318 | A1 | 5/2006 | Davidson |

FOREIGN PATENT DOCUMENTS

| | | | |
|---|---|---|---|
| JP | 57-45833 | | 3/1982 |
| JP | 04109927 | | 8/1990 |
| JP | 04109927 | | 4/1992 |
| JP | 4-144533 | | 5/1992 |
| JP | 1992-144533 | | 5/1992 |
| JP | 2000-047651 | | 2/2000 |
| JP | 2000047651 | A * | 2/2000 |
| WO | WO 99/40587 | | 8/1999 |
| WO | 00-22975 | | 4/2000 |
| WO | WO 01/50180 | | 7/2001 |
| WO | WO 01/50941 | | 7/2001 |
| WO | WO 01/65995 | | 9/2001 |
| WO | 02/054932 | A2 | 7/2002 |
| WO | WO 02/054932 | | 7/2002 |
| WO | 2005062715 | A2 | 7/2005 |

OTHER PUBLICATIONS

Copy of Supplimentary European Search Report for Application No. EP03 70 6877 Date of completion Jul. 26, 2006.
Office Action dated Oct. 27, 2006 U.S. Appl. No. 10/610,915.
"Synchronized nQUAD Technology", www.cartesiantech.com.
Yang et al., "Two Image Photometric Stereo Method", SPIE, vol. 1826, Intelligent Robots and Computer Vision XI, 1992.
Office Action for U.S. Appl. No. 10/986,918, dated Sep. 22, 2005.
Office Action for U.S. Appl. No. 10/986,918 dated Apr. 6, 2006.
U.S. Appl. No. 60/533,263, filed Dec. 31, 2003, Meron et al.
U.S. Appl. No. 10/986,918, filed Nov. 15, 2004, Davidson.
Japanese Office Action for Application No. 2003-568895 dated Sep. 3, 2007.
Jun Yang, Noboru Ohnishi, Noboru Sugie, "Two Image Photometric Stereo Method", Department of Information Engineering, Nagoya University, SPIE vol. 1826 Intelligent Robots and Computer Vision XI (1992) pp. 452-463.
synQUAD Technology Synchronized nQUAD Technology printed Mar. 15, 2000.
International Search Report of PCT/IL03/00110 dated Jul. 7, 2003.
International Search Report of PCT/IL04/01181 dated Feb. 24, 2006.
Final Office Action for U.S. Appl. No. 10/610,915 dated May 17, 2007.
Final Office Action for U.S. Appl. No. 10/986,918 dated Apr. 6, 2006.
Office Action for U.S. Appl. No. 10/986,918 dated Sep. 22, 2005.

* cited by examiner

SYSTEM AND METHOD FOR DISPLAYING AN IMAGE STREAM

PRIOR PROVISIONAL PATENT APPLICATION

The present application claims benefit from prior provisional patent application Ser. No. 60/355,796 filed on 12 Feb. 2002 and entitled "SYSTEM AND METHOD FOR VIEWING A MOVING IMAGE", incorporated herein by reference in its entirety.

FIELD OF THE INVENTION

The present invention relates to a method and system for displaying and/or reviewing image streams. More specifically, the present invention relates to a method and system for effective displaying of an image stream.

BACKGROUND OF THE INVENTION

An image stream may be assembled from a series of still images and displayed to a user. The images may be created or collected from various sources. For example, U.S. Pat. No. 5,604,531 to Iddan et al., assigned to the common assignee of the present application and incorporated herein by reference, teaches an in-vivo imager system which in one embodiment includes a swallowable capsule. The imager system captures images of a lumen such as the gastrointestinal (GI) tract and transmits them to an external recording device while the capsule passes through the lumen. Large numbers of images may be collected for viewing and, for example, combined in sequence. An image stream of, for example, 40 minutes in length, containing for example about 4,800 frames, may be presented to the user for review. Other numbers of frames or lengths may be used.

In one embodiment, a streaming rate is preset, but the user can increase or decrease the streaming rate at anytime during the review process, and/or define a different streaming rate. In general, a user may try to set the streaming rate to the highest rate where the user can quickly and effectively review the image stream without missing important information that may be present in any of the images included in the stream. The rate at which a user can effectively review a image stream is limited by a physiological averaging effect that is known to exist at around 15 frames per second (although this number varies for different users and image streams) above which certain details in individual images displayed in the stream may be physiologically filtered out.

Therefore, a need exists for a system and method that enables a user to increase the rate at which the user can efficiently and effectively review an image stream.

SUMMARY OF THE INVENTION

In one embodiment, a system and method are provided for displaying an image stream, where an original image stream is divided into two or more images streams, each image stream being displayed simultaneously or substantially simultaneously. When used herein, "substantially simultaneously" includes simultaneously and almost simultaneously. A system and method according to one embodiment of the invention enables a user to see images in the stream for a longer period of time without increasing the overall viewing time of the entire image stream. Alternatively, the system and method described according to one embodiment may be used to increase the rate at which a user can review the image stream without sacrificing details that may be depicted in the stream. In certain embodiments, the images are collected from a swallowable capsule traversing the GI tract.

BRIEF DESCRIPTION OF THE DRAWINGS

The present invention will be understood and appreciated more fully from the following detailed description taken in conjunction with the drawings in which.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Figure 1:
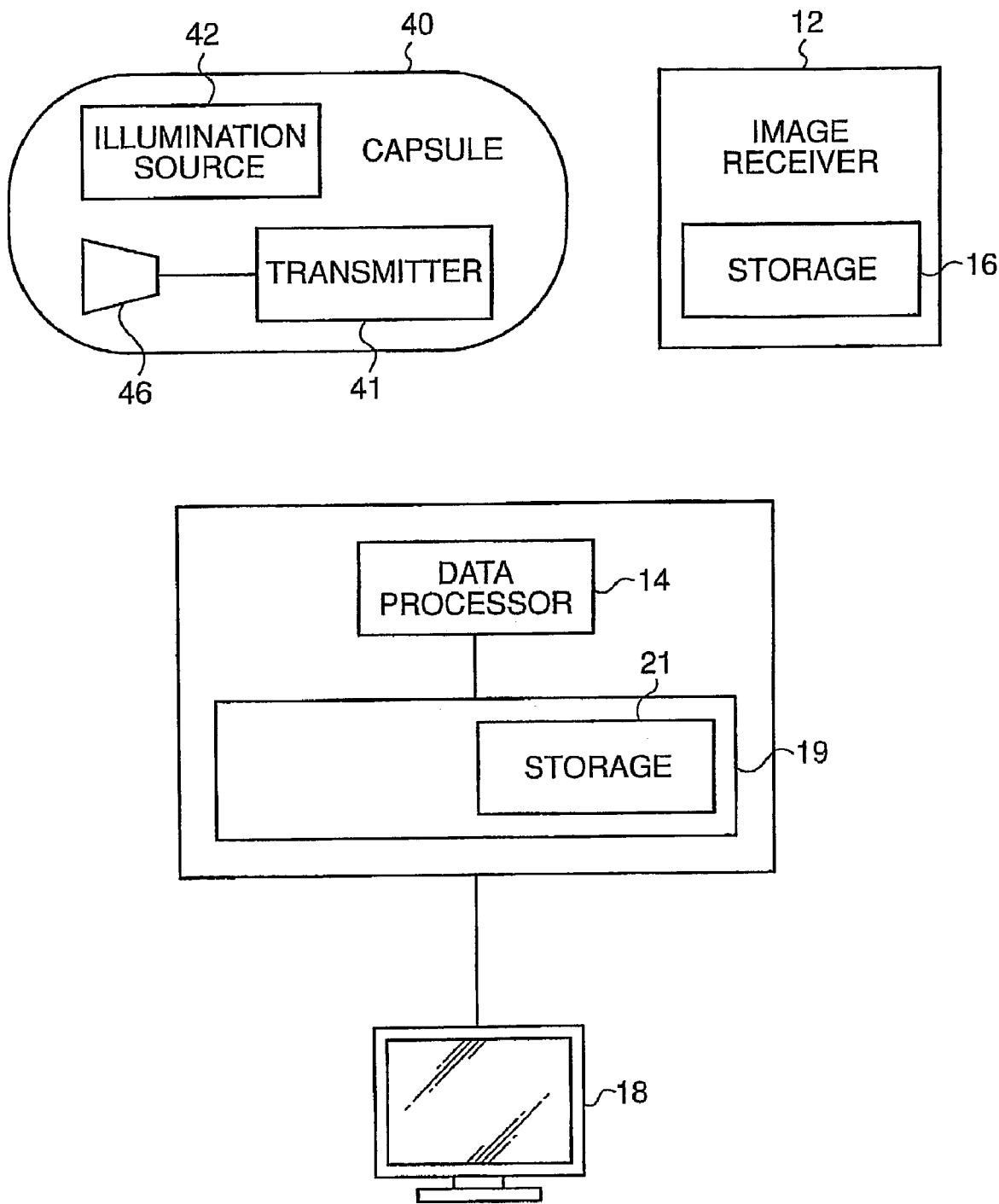
FIG. 1 shows a schematic diagram of an in-vivo imaging system according to one embodiment of the present invention.

Reference is made to FIG. 1, which shows a schematic diagram of an in-vivo imaging system according to one embodiment of the present invention. In an exemplary embodiment, the system comprises a capsule 40 having an imager 46, for capturing images, an illumination source 42, for illuminating the body lumen, and a transmitter 41, for transmitting image and possibly other information to a receiving device. Typically, the image capture device may correspond to embodiments described in U.S. Pat. No. 5,604,531 to Iddan et al., and to embodiments described in published application WO01/65995 to Glukhovsky et al., but in alternate embodiments may be other sorts of image capture devices.

Typically, located outside the patient's body in one or more locations are an image receiver 12, typically including an antenna or antenna array (not shown), an image receiver storage unit 16, a data processor 14, a data processor storage unit 19, and an image monitor 18, for displaying, inter alia, images recorded by the capsule 40. Typically, data processor storage unit 19 includes an image database 21.

Typically, data processor 14, data processor storage unit 19 and monitor 18 are part of a personal computer or workstation, which includes standard components such as processor 14, a memory, a disk drive, and input-output devices, although alternate configurations are possible. Data processor 14 may include any standard data processor, such as a microprocessor, multiprocessor, accelerator board, or any other serial or parallel high performance data processor. Data processor 14 typically, as part of its functionality, acts as a controller controlling the display of the images. Image monitor 18 is typically a conventional video display, but may, in addition, be any other device capable of providing image or other data. The image monitor 18 presents the image data, typically in the form of still and moving pictures, and in addition may present other information. In an exemplary embodiment, the various categories of information are displayed in windows. Multiple monitors may be used to display image and other data.

In operation, imager 46 captures images and sends data representing the images to transmitter 41, which transmits images to image receiver 12 using, for example, electromagnetic radio waves. Image receiver 12 transfers the image data to image receiver storage unit 16. After a certain period of time of data collection, the image data stored in storage unit 16 is sent to the data processor 14 or the data processor storage unit 19. For example, the image receiver 12 or image receiver storage unit 16 may be taken off the patient's body and connected to the personal computer or workstation which includes the data processor 14 and data processor storage unit 19 via a standard data link, e.g., a serial, parallel, USB, or wireless interface of known construction. The image data is then transferred from the image receiver storage unit 16 to an image database 21 within data processor storage unit 19. Typically, the image stream is stored as a series of images in the image database 21, which may be implemented in a variety of known manners. Data processor 14 may analyze the data and provide the analyzed data to the image monitor 18, where a user views the image data. Data processor 14 operates software (not shown) that, in conjunction with basic operating software such as an operating system and device drivers, controls the operation of data processor 14. Typically, the software controlling data processor 14 includes code written in the C++ language, but may be implemented in a variety of known methods. Data processor 14 may include graphics software or hardware.

The image data collected and stored may be stored indefinitely, transferred to other locations, or manipulated or analyzed. A health professional may, for example, use the images to diagnose pathological conditions of the GI tract, and, in addition, the system may provide information about the location of these pathologies. While, using a system where the data processor storage unit 19 first collects data and then transfers data to the data processor 14, the image data is not viewed in real time, other configurations allow for real time viewing.

Typically, the in-vivo imager system collects a series of still images as it traverses the GI tract. The images may be later presented as a stream of images of the traverse of the GI tract. The in-vivo imager system may collect a large volume of data, as the capsule 40 may take several hours to traverse the GI tract, and may record images at a rate of, for example, two images every second, resulting in the recordation of thousands of images. The image recordation rate (or frame capture rate) may be varied.

Typically, the image data recorded and transmitted by the capsule 40 is digital color image data, although in alternate embodiments other image formats may be used. In an exemplary embodiment, each frame of image data includes 256 rows of 256 pixels each, each pixel including bytes for color and brightness, according to known methods. For example, in each pixel, color may be represented by a mosaic of four sub-pixels, each sub-pixel corresponding to primaries such as red, green, or blue (where one primary is represented twice). The brightness of the overall pixel is recorded by a one byte (i.e., 0-255) brightness value. Typically, images are stored sequentially in data processor storage unit 19. The stored data is comprised of one or more pixel properties, including color and brightness. Other image formats may be used.

Typically, data processor storage unit 19 stores a series of images recorded by a capsule 40. The images the capsule 40 records, for example, as it moves through a patient's GI tract may be combined consecutively to form a series of images displayable as an image stream. When viewing the image stream, the user is typically presented with one or more windows on monitor 18; in alternate embodiments multiple windows need not be used and only the image stream is displayed. In an embodiment where multiple windows are provided, for example, an image window may provide the image stream, or still portions of that image. Another window may include buttons or other controls that may alter the display of the image; for example, stop, play, pause, capture image, step, fast-forward, rewind, or other controls. Such controls may be activated by, for example, a pointing device such as a mouse or trackball. Typically, the image stream may be frozen to view one frame, speeded up, or reversed; sections may be skipped; or any other method for viewing an image may be applied to the image stream.

While the following discussion relates to the case where data from a capsule 40 is stored for later use, the system and method of the present invention may be used with systems allowing for real time viewing of image data.

While, typically, information gathering, storage and processing are performed by certain units, the system and method of the present invention may be practiced with alternate configurations. For example, the components gathering image information need not be contained-in a capsule, but may be contained in any other vehicle suitable for traversing a lumen in a human body, such as an endoscope, stent, catheter, needle etc.

In another embodiment, information gathering can be performed in another cavity besides a lumen in a human body. An example can include information gathered in an animal lumen. Another example can include information gathered from pipes or other cavities formed during a manufacturing process. Yet another example can be information gathered through a natural stream, for example, geological or marine formations.

Furthermore, while typically the components accepting, processing and displaying the image data are contained within a workstation system or PC, other systems may be used, and other (e.g., distributed) components may perform such image accepting, processing and displaying.

In one embodiment, the image stream may be presented to the viewer as multiple image streams in two or more windows, such that as the image streams are displayed a set of consecutive or "nearby" frames are displayed substantially simultaneously. For example, in one embodiment, two windows or viewing areas are displayed, each displaying one frame of an image stream. Typically, the frames are displayed substantially simultaneously. According to one embodiment, in each time slot, two images which are consecutive in the image stream are displayed, one in each window or viewing area. For example, in one embodiment, the image stream is divided into two separate streams that are displayed substantially simultaneously. Frames, which are consecutive or adjacent in the original stream, become in the separate streams, corresponding frames (e.g., the first frame in each corresponding stream, the second frame in each corresponding stream). Thus, when the two resulting streams are displayed, frames 1 and 2 from the original stream may be displayed side by side, then frames 3 and 4, etc. In another embodiment the image stream is divided into three or more separate streams that are displayed substantially simultaneously. In yet another embodiment some frames in the stream maybe skipped.

In an exemplary embodiment, the windows or viewing areas are close together, with a minimum of blank or black space between the images, and typically horizontally and side by side, to allow a viewer to see the entirety of the images without substantially moving his eyes. The images may be distorted (e.g., displayed in a cone, oval or ellipse shaped field) to further reduce the space between them. The images may be displayed with symmetry. For example, the images may be displayed in the same horizontal plane. One image may be reversed and presented as a mirror image, the images may have their orientation otherwise altered, or the images may be otherwise processed to increase symmetry.

Typically, if normally the image stream is displayed at a certain rate, the two separate image streams displayed according to one embodiment may each be displayed at half that speed. Thus, if the image stream may be displayed at 20 frames per second each of the two streams may be displayed at 10 frames per second. In such a case the same number of overall frames per second is displayed, but the user can view twice as much information for twice as long. The total display time for the image streams is the same as that of the original image stream, but each frame is displayed to the user for a longer period of time. In another example, if a user is comfortably viewing a single image stream at one rate, adding a second stream will allow the user to increase the total review rate without reducing the time that each frame is displayed. In alternate embodiments, the relationship between the display rate when the image stream is displayed as one image stream and when it is displayed as multiple streams may differ; for example, the resulting multiple image streams may be displayed at the same rate as the original image stream.

Figure 2:
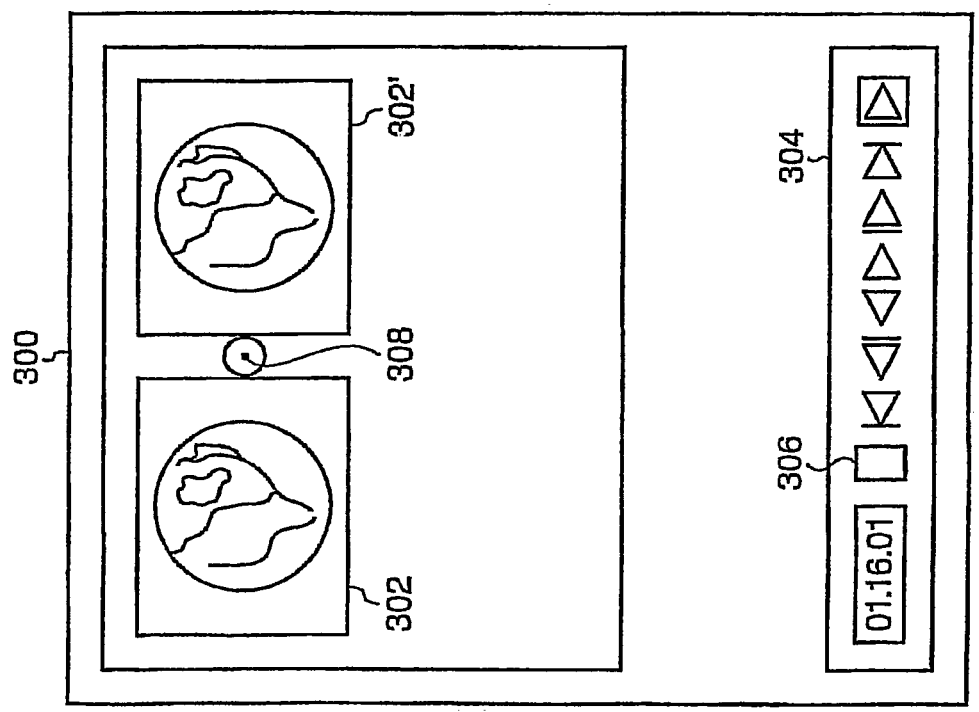
FIG. 2 depicts a portion of a display according to an embodiment of the present invention.

In an exemplary embodiment, the user may switch modes, between viewing the images as one stream and viewing the images as multiple streams using a control such as a keystroke or on-screen button. The user may control the multiple streams in a manner similar to the control of a single stream, for example by using on screen controls. In an alternate embodiment, only one mode may be offered to the user. FIG. 2 depicts a portion of a display according to an embodiment of the present invention. Referring to FIG. 2, the display 300 is in multiple image stream mode. The display 300 may be displayed on, for example, image monitor 18. Typically, the display 300 includes a set of image windows 302 and 302', for displaying image streams, and a set of controls 304. The controls 304 may include, for example, a toggle control 306, allowing the user to toggle between a multiple image stream mode and a single image stream mode. The controls 304 may also include, for example, conventional video controls, such as pause, stop, play, fast-forward, reverse, etc. In a typical embodiment, if the system is in a multiple image stream mode, the controls 304 act on all image streams simultaneously; in alternate embodiments, other methods may be used, for example the controls 304 may act on a single image stream.

As seen in FIG. 2, two image streams are displayed. Typically, at any one time, since the images in each image stream are substantially adjacent, since adjacent images are typically similar, and since each image stream is displayed synchronously (e.g., the frame having the same or similar frame number is displayed for each), the images displayed in window 302 and 302' are substantially similar. Typically, a user viewing multiple image streams directs the center of his vision to a point in-between the image streams, e.g., point 308. Typically point 308 is not displayed on the monitor 18 (but may be); point 308 is included in FIG. 2 for illustrative purposes. The user may absorb the relevant information about the image streams in such a manner; such viewing may require a period of training. For example, if the image streams are of the GI tract, the user may, by directing his gaze to point 308, absorb information regarding pathologies from the set of image windows.

In alternate embodiments, the different image streams may be placed in different configurations on a viewing screen. For example, rather than horizontally, the image streams may be arranged vertically or diagonally. In further embodiments, different numbers of image streams may be displayed. For example, if three image streams are to be displayed simultaneously, frames 1, 2 and 3 of the original stream may be displayed, then frames 4, 5 and 6, etc. In further embodiments, adjacent frames need not be displayed, and the frames may not be displaying the specific patterns discussed herein. For example, certain frames may be skipped: frames 1 and 6 may be displayed, then frames 3 and 8, etc. Frames that are substantially adjacent, rather than immediately adjacent (e.g., frames 1 and 5 ), may be displayed simultaneously. The frames in different image streams need not be displayed simultaneously; the frames may be displayed at different times or independently.

Various methods may be used to separate an original image stream into one or more secondary image streams to be displayed. In one embodiment, images from the original image are simply directed to the proper screen position at viewing time, and the image stream is not actually separated; in alternate embodiments, the images may be separated for example, placed in different files or memory blocks. In one embodiment, each resulting image stream includes a separate subset of images from the original image stream; in alternate embodiments, the images from each resulting image stream may overlap. Subset image streams may include different images from the original stream in different embodiments.

In certain embodiments of the present invention, more than one image stream may be collected. For example, an in-vivo vehicle may include more than one imager (or one imager) collecting multiple image streams—possibly by including an imager or lens system in more than one location on the vehicle. Capsule 40 may include more than one imager 46. The imagers 46 may be arranged, for example, at either end of the capsule 40, or at the same end of the capsule, in slightly different positions or different angles. A capsule which includes a plurality of imagers is described, for example, in International Publication Number WO 02/054932 which is assigned to the common assignee of the present application. Each imager 46 may capture images and transmit the images via the transmitter 41 or via separate transmitters. Typically, each imager 46 has associated an optical system. In such a case, an embodiment of the system and method of the present invention may display each image stream simultaneously, where each image displayed on the viewer screen was typically captured at the same time. In one embodiment, images from each of the imagers can be displayed substantially simultaneously so that image streams from different imagers can be reviewed simultaneously. In another embodiment, image streams from each imager may be divided into a number of subset image streams and the subset image streams for one or more imagers may be shown substantially simultaneously. E.g., one subset image stream may include every other image frame whereas the second subset stream may include every other consecutive image frame (e.g. the first subset includes frames 1,3,5 etc and the second subset includes frames 2,4,6 etc.). Typically, in such a case images may be shown in matrix form so that each column may display frames from a single imager and each row may display frames from a different imager. Alternatively, each row may display frames from a single imager and each column may display frames from a different imager. In further embodiments, an image stream may be divided up or partitioned into sections, rather than based on substantially adjacent frames. For example, an image stream may be divided into a first section and a second section, where the first and second section are sequential. The two sections may be displayed simultaneously. More sections or partitions may be created.

In an exemplary embodiment, the windows or viewing areas are close together, with a minimum of blank or black space between the images, and are typically horizontally and side by side, to allow a viewer to see the entirety of the images without substantially moving his eyes. The images may be distorted (e.g., displayed in a cone, oval or ellipse shaped field) to further reduce the space between them. The images may be displayed with symmetry. For example, the images may be displayed in the same horizontal plane. One image may be reversed and presented as a mirror image, the images may have their orientation otherwise altered, or the images may be otherwise processed to increase symmetry. Typically, a tool available to the user which manipulates an image (e.g., region of interest or zoom) will have an identical effect on all images simultaneously displayed. Each image may be displayed with different post-processing. For example, one image may be subject to certain filtering or manipulation (e.g., red or green filtering, contrast enhancement, brightness alteration) and the other image may be subject to different or no filtering or manipulation.

In another embodiment a still image can be displayed substantially adjacent to the image streams so that the image streams can be easily compared to the still image during the viewing process. In yet another embodiment, an image stream obtained form an imager is displayed substantially simultaneously and substantially adjacent to an image stream obtained from an ultrasound, temperature and/or a pH imager. Displaying image streams or single images substantially simultaneously, from different types of imagers may help to draw a users attention to frames that may show abnormalities and/or pathologies.

In alternate embodiments, the system and method of the present invention may operate on image streams having alternate formats, on image streams being from alternate sources capsule, and containing images from sites other than the GI tract.

Embodiments of the present invention may allow an image stream to be viewed as a smoother moving image, with less jitter by reducing the rate at which each image in the set of images displayed substantially simultaneously are streamed, without decreasing the original stream rate. In some cases, if concurrently displayed images differ in a certain manner, the viewer may be able to more easily spot pathologies or other conditions.

Figure 3:
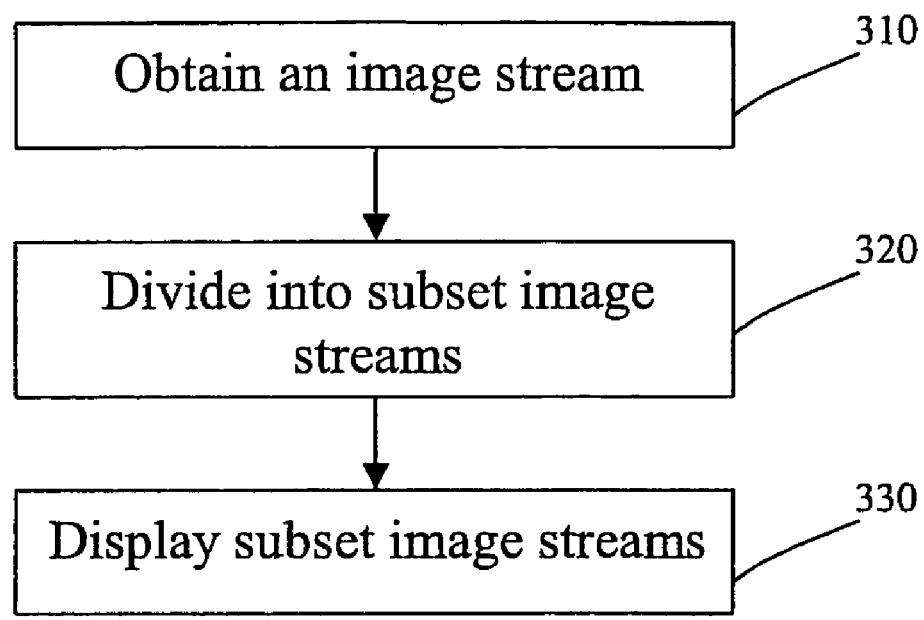
FIG. 3 is a flow chart of a method for viewing an image stream according to an embodiment of the invention.

According to an embodiment of the invention a method for viewing an image stream includes the step of displaying an original image stream as a plurality of image streams. Reference is now made to FIG. 3, which schematically illustrates a method according to one embodiment of the invention. According to one embodiment an original stream of images is obtained (step 310), for example, by using images obtained by an imaging capsule that traverses the GI tract while acquiring-images of the GI tract. The original image stream is then divided into a plurality of subset image streams (step 320), each subset including at least a portion of the original image stream. According to one embodiment, frames, which are consecutive or adjacent in the original stream, become in the separate streams, corresponding frames (e.g., the first frame in each corresponding stream, the second frame in each corresponding stream). Thus, when the two resulting streams are displayed, frames 1 and 2 from the original stream may be displayed side by side, then frames 3 and 4, etc. The subset streams are displayed on a display (step 330) preferable substantially simultaneously, typically for observing and/or analyzing, for example, for detecting pathologies in the GI tract. In one embodiment of the invention, the main display engine is programmed to select the next two images to be displayed substantially at the same time (instead of the next image), and a display window displays those two images at the substantially the same time, until the next two images are selected from the display engine.

In one embodiment of the system and method of the present invention, an image stream is displayed to the user in a manner reducing jitter, smoothing the presentation, and allowing easier and more pleasant viewing of the image stream. In such an embodiment, additional intermediate images are formed and inserted into the image stream, the intermediate images being formed from combinations of adjacent or substantially adjacent images. In one embodiment, the combinations are created by morphing or averaging adjacent images so that the resulting additional image is, when viewed as part of a moving image stream, somewhere intermediate in time to the two original images. In alternate embodiments other methods of combining images may be used. In one embodiment, synthesizing methods such as those used in the MotionPerfect® software provided by DynaPel of Germany may be used. Such methods use motion information from the moving image stream to interpolate data for additional image frames. Other interpolation or synthesizing methods may be used.

The system and method of the present invention may allow an image stream to be viewed in an efficient manner and over a shorter time period.

It will be appreciated by persons skilled in the art that the present invention is not limited by what has been particularly shown and described hereinabove. Rather the scope of the invention is defined by the claims that follow.

The invention claimed is:

1. A method for displaying an image stream obtained from a swallowable capsule, the method comprising:
   creating an original image stream from images received from a swallowable capsule;
   displaying images from the original image stream across a plurality of consecutive time slots;
   wherein in each time slot a set of consecutive images from the original image stream is displayed, each image within the set being displayed at the same time;
   wherein the set of consecutive images displayed in each time slot is immediately consecutive, in the original image stream, to the set of consecutive images in the immediately previous time slot;
   thereby increasing the rate at which the original image stream can be reviewed without reducing image display time.

2. The method according to claim 1 wherein the set of consecutive images consists of two images.

3. The method according to claim 1 wherein the original image stream is obtained from within a body lumen.

4. The method according to claim 3 wherein the body lumen is in the gastrointestinal tract.

5. The method of claim 1, wherein each image in the set of consecutive images from the original image stream is displayed in a separate viewing area.

6. The method of claim 1, wherein each set of consecutive images consists of two images.

7. The method of claim 1 comprising:
   displaying the original image stream; and
   switching to displaying images from the original image stream across a plurality of consecutive time slots, wherein in each time slot a set of consecutive images from the original image stream is displayed, each image within the set being displayed at the same time.

8. The method of claim 1 comprising:
   displaying an on-screen button to switch between:
   displaying the original image stream; and displaying images from the original image stream across a plurality of consecutive time slots, wherein in each time slot a set of consecutive images from the original image stream is displayed, each image within the set being displayed at the same time.

9. A system for displaying an image stream, the system comprising:

an image storage memory capable of accepting images acquired by a swallowable capsule, the images forming an original image stream; and an image display controller to display images from the original image stream across a plurality of consecutive time slots:

wherein in each time slot a set of consecutive images from the original image stream is displayed, each image within the set being displayed at the same time;

wherein the set of consecutive images displayed in each time slot is immediately consecutive, in the original image stream, to the set of consecutive images in the immediately previous time slot;

thereby increasing the rate at which the original image stream can be reviewed without reducing image display time.

10. The system according to claim 9 wherein the original image stream is obtained from within a body lumen.

11. The system according to claim 10 wherein the body lumen is in the gastrointestinal tract.

12. The system according to claim 9, wherein each image in the set of consecutive images from the original image stream is displayed in a separate viewing area.

13. The system of claim 9, wherein each set of consecutive images consists of two images.

* * * * *